(12) United States Patent
Peppel

(10) Patent No.: US 8,298,195 B2
(45) Date of Patent: Oct. 30, 2012

(54) NEEDLELESS ACCESS PORT VALVE

(75) Inventor: Peter W. Peppel, Nazareth, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 787 days.

(21) Appl. No.: 11/877,569

(22) Filed: Oct. 23, 2007

(65) Prior Publication Data

US 2009/0105666 A1   Apr. 23, 2009

(51) Int. Cl.
*A61M 5/00* (2006.01)
(52) U.S. Cl. .......................... 604/249; 604/246
(58) Field of Classification Search .......... 604/246–256; 29/890.127, 458; 251/149.1, 149.6
See application file for complete search history.

(56) References Cited

U.S. PATENT DOCUMENTS

| 5,699,821 A * | 12/1997 | Paradis .............................. 137/1 |
| 6,871,838 B2 * | 3/2005 | Raines et al. ............... 251/149.4 |
| 2006/0217671 A1 * | 9/2006 | Peppel .......................... 604/246 |
| 2010/0308251 A1 * | 12/2010 | Pascal et al. .................. 251/324 |

* cited by examiner

*Primary Examiner* — Kevin C Sirmons
*Assistant Examiner* — Imani Hayman
(74) *Attorney, Agent, or Firm* — Klein, O'Neill & Singh, LLP

(57) ABSTRACT

Needleless access port valves are generally discussed herein with particular discussions extended to needleless access port valves having a resilient piston. The valve includes a valve housing having an inlet port, an outlet port, and an interior cavity with an upper shoulder and a lower shoulder. A resilient piston made of a homogeneous material is positioned within the interior cavity and is compressed by the upper shoulder and the lower shoulder of the valve housing.

20 Claims, 2 Drawing Sheets

NEEDLELESS ACCESS PORT VALVE

Needleless access port valves are generally discussed herein with particular discussions extended to needleless access port valves comprising a resilient piston.

BACKGROUND

Needleless access port valves are widely used in the medical industry for accessing an intravenous (IV) line and/or the internals of a patient or subject. Generally speaking, prior art valves utilize a valve housing in combination with a moveable internal plug or piston to control the flow of fluid through the valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a needleless access port valve comprising a valve housing comprising an inlet port, an outlet port, and an interior wall surface defining an interior cavity. A resilient piston made of a homogeneous material is positioned within the interior cavity. The piston has a solid upper section of a first diameter, a neck section of a second diameter, which is larger than the first diameter, and a mid-section of a third diameter, which is larger than the second diameter. The interior cavity comprises an upper shoulder, a lower shoulder, and a plurality of flow passages for fluid flow between the piston and the interior wall surface of the housing. The neck section of the piston is compressed by the upper shoulder of the housing, and the mid-section of the piston is compressed by the lower shoulder of the valve housing to terminate fluid communication between the inlet port and the outlet port.

In another embodiment of the present invention, a needleless access port valve comprises a valve housing comprising an inlet port adapted to receive a medical implement, an outlet port, and an interior cavity having an upper shoulder and a lower shoulder. The upper shoulder comprises one or more upper flow channels, and the lower shoulder comprises one or more lower flow channels. A resilient piston made of a homogeneous material is positioned within the interior cavity. The piston has a neck section and an enlarged mid-section. A top surface of the neck section comprises a generally planar surface positioned at an angle to a planar surface defined by an opening of the inlet port when in a closed position. The neck section is compressed by the upper shoulder, and the enlarged mid-section is solid and is compressed by the lower shoulder of the valve housing.

In yet another embodiment of the present invention, a needleless access port valve comprises a housing comprising a top opening, an outlet port having a bottom opening, and a hollow interior having an upper raised portion and a lower raised portion. The top opening is adapted to receive a medical instrument, and the bottom opening is adapted to communicate with an intravenous tube. Means for biasing is located within the hollow interior, is formed of a homogeneous material, and has a stem projecting from a lower end. The stem projects into and occupies at least a portion of the outlet port. The means for biasing is compressed by the upper and lower raised portions of the hollow interior, and is adapted to open a fluid pathway between the hollow interior and the medical instrument when the means for biasing is compressed by the medical instrument. The means for biasing forms a seal with the housing, and the seal prevents fluid flow between the top and bottom openings in a closed position.

Other features and variations of the valve assemblies summarized above are also contemplated and will be more fully understood when considered with respect to the following disclosure.

BRIEF DESCRIPTION OF THE DRAWINGS

These and other features and advantages of the present invention will become appreciated as the same become better understood with reference to the specification, claims and appended drawings wherein:

DETAILED DESCRIPTION

The detailed description set forth below in connection with the appended drawings is intended as a description of the presently preferred embodiments of needleless access port valves or backcheck valves (herein "valves") provided in accordance with the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

Figure 1:
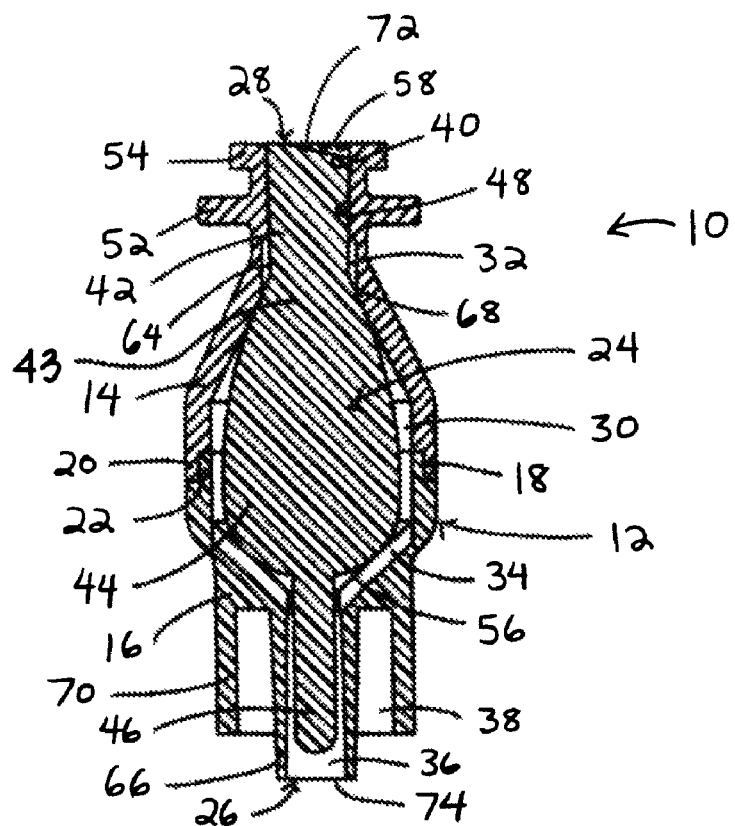
FIG. 1 is a cross-sectional side view of a needleless access port valve in an embodiment of the present invention, shown in a closed position.

FIG. 1 shows a cross-sectional side view of a needleless access port valve 10 in an embodiment of the present invention. The valve 10 is shown in a closed position. In one embodiment, the valve 10 comprises a valve housing 12 comprising an upper housing section 14 and a lower housing section 16. The upper and lower housing sections 14 and 16 may be formed from a rigid plastic material, such as polycarbonate, polyurethane, or the like. In one exemplary embodiment, one or more colors are incorporated into the material.

Preferably, the material has a translucent pantone green tone. Alternatively, an opaque material with one or more color tones may also be incorporated.

The upper housing section 14 includes a receiving end 20 that functions like a socket for receiving a male projection 22 on the lower housing section 16 at an interface 18 of the two housing sections. The socket 20 and male projection 22 are coupled together at the interface 18 to form the valve housing 12. The socket 20 and male projection 22 may be attached to one another in a friction fit as shown, a threaded fit, or other methods known to those skilled in the art, such as laser or ultrasonic welding. The valve housing 12 further comprises an inlet port 28 having an inlet opening 72, an outlet port 26 having an outlet opening 74, and an interior cavity 30. Fluid is introduced at the inlet port 28 via a medical implement, such as a syringe, and then flows through the valve 10 and exits the outlet port 26. Alternatively, a fluid or blood sample can be withdrawn through the valve 10, such that fluid flows in the direction from the outlet port 26 to the inlet port 28.

In one exemplary embodiment, the upper housing section 14 comprises an upper interior wall 48 or upper interior neck section, exterior threads 54, and a stop flange 52 for limiting thread engagement with a corresponding male threaded luer. Alternatively, the flange may be omitted and the Luer taper of the inlet port 28 and the corresponding Luer taper of a medical implement can provide a physical stop. The upper housing section 14 further comprises an upper flow channel 32. In exemplary embodiments of the invention, a plurality of upper flow channels 32 are provided. In the particular embodiment shown in FIG. 1, the upper housing section 14 comprises eight upper flow channels 32. The channels 32 may be formed by molding spaced-apart indentations into the upper interior neck section of the upper housing section 14. In a preferred embodiment, the eight upper flow channels 32 are equally spaced apart from one another.

The lower housing section 16 comprises a tapered wall or shoulder 56, which resembles a frusto-conical section having at least one flow channel 34. In exemplary embodiments of the invention, a plurality of lower flow channels 34 are provided. In the particular embodiment shown in FIG. 1, the lower housing section 16 comprises eight spaced-apart lower flow channels 34 formed by molding indentations into the interior frusto-conical section of the lower housing section 16. In a preferred embodiment, the lower flow channels 34 are equally spaced apart from one another. The lower housing section 16 further comprises an outer wall or collar 70 forming an annular space 38, and an outlet nozzle 66 forming an outlet passage 36. The collar 70 and annular space 38 are adapted to receive a female luer from an IV set, a tubing, a catheter assembly, or the like (not shown), which carries fluid to or from the patient. Although not shown, the collar 70 may incorporate internal threads for threaded engagement with a threaded female luer.

A piston 24 is positioned in the interior cavity 30 of the valve housing 12. The piston 24 comprises an upper plug section 42, neck section 43, a bulbous midsection 44, and a lower stem section 46. The upper plug section 42 comprises a circumferential exterior wall surface 64 adapted to contact the interior wall 48 of the upper housing section 14. The upper plug section 42 also comprises a tapered top surface 40 for providing a fluid flow space between the top surface of the piston 24 and a circumferential end of a medical implement. A gap 58 is formed at the inlet opening 72 due to the relative geometries between the tapered surface 40 and the inlet opening 72. In one exemplary embodiment, the piston 24 is formed of a resilient and pliable material capable of substantially recovering its size and shape when deflected or compressed.

In a preferred embodiment, the piston 24 is integrally formed from a thermoplastic elastomer (TPE). More particularly, the piston 24 is formed from a silicone elastomer. While a piston 24 formed of a resilient material is described in this embodiment and is more preferred, other resilient elements may be used, such as a spring disposed internally of a piston having a hollow interior cavity.

In another aspect of the present invention, the piston 24 may be molded with one or more bores to facilitate compression. For example, the one or more bores can be formed near the stem 46 and in a generally vertical configuration, relative to an axis define between the inlet port and the outlet port. The one or more bores may also be formed horizontally relative to the axis. More preferably, the one or more bores are formed at an inclined angle to the axis so that as the piston is compressed, fluid trapped inside the one or more bores, if any, may drain out of the one or more bores, which is facilitated by the compressing piston. The bores can have any shape and are preferably tapered so that portions located deep inside the piston, i.e., away from the exterior surface of the piston, are sufficiently compressed when the piston is compressed to push out any trapped fluid.

When the valve 10 is in the closed position, shown in FIG. 1, the top of the tapered surface 40 of the piston 24, more particularly the generally planar surface of the top surface, is preferably flush with the inlet opening 72, except for the gap 58. This configuration allows the top 40 to be swabbed or sanitized. Due to the relative dimensions of the piston 24 and the internal cavity 30 of the housing 12, the circumferential exterior wall surface 64 of the upper plug section 42 is urged against the interior wall 48 of the upper housing section 14. The resiliency of the piston 24 provides a fluid tight contact between the upper plug section 42 and the interior wall 48 and is configured to terminate fluid communication between the inlet port 28 and the outlet port 26. The bulbous midsection 44 of the piston 24 occupies the interior cavity 30 and is urged against the tapered wall 56 of the lower housing section 16 and against a shoulder 68 of the upper housing section 14. In this closed position, a first seal point is formed between the upper interior wall 48 and the circumferential exterior wall surface 64 of the piston, and a second seal point is formed between the shoulder 68 and the upper part of the bulbous midsection 44 to terminate fluid communication between the inlet port 28 and the outlet port 26.

Figure 2:
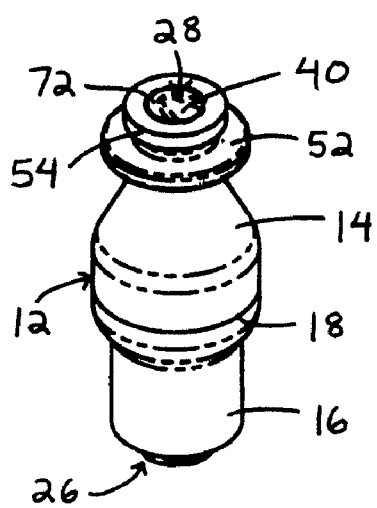
FIG. 2 is a perspective view of the valve of FIG. 1.

Referring now to FIG. 2, a perspective view of the valve of FIG. 1 is shown. The tapered top surface 40 of the piston 24 is visible through the inlet opening 72. The housing 12 includes the interface 18 between the upper housing section 14 and the lower housing section 16. The outlet port 26 is visible at the bottom of FIG. 2. Although not shown, labels, aesthetic indicia, and/or ribs or projections for gripping may be incorporated on the exterior surface of the valve housing 12.

Figure 3:
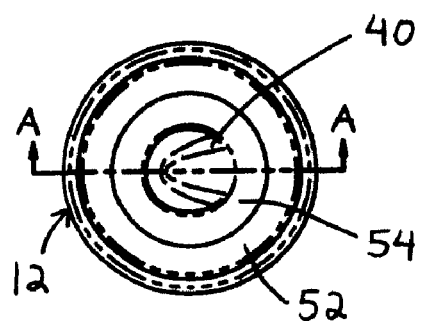
FIG. 3 is a cross-sectional top view of the valve of FIG. 1.

FIG. 3 is a cross-sectional top view of the valve of FIG. 1. The line AA in FIG. 3 shows the plane of the cross-sectional view of FIG. 1. FIG. 3 also shows the tapered top surface 40 of the piston 24, the exterior threads 54, and the stop flange 52.

Figure 4:
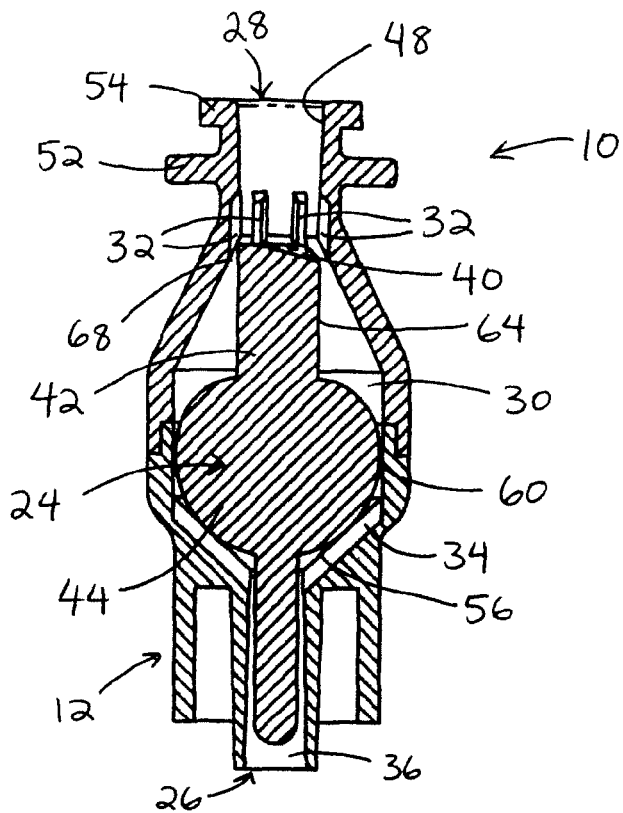
FIG. 4 is a cross-sectional side view of the valve of FIG. 1 in an open position.

FIG. 4 is a cross-sectional side view of the valve of FIG. 1 in an open position. A medical implement (not shown) is introduced at the inlet port 28 to compress the piston 24 into the open position. When the medical implement compresses the piston 24, the bottom tip of the medical implement urges against the tapered top surface 40 of the piston 24. The tapering of the surface 40 provides a flow space or gap for fluid flow from the medical implement to flow out of the medical implement and into the valve 10. Without tapering, the contact between the top surface 40 of the piston 24 and the medical implement could block fluid flow from the implement into the valve 10. Although tapering is described in this particular embodiment, other methods of creating a gap between the piston 24 and the medical implement can be used, such as forming grooves or channels in the top surface 40.

When the medical implement compresses the piston 24, the upper flow channels 32 are exposed. Fluid flows from the medical implement through the upper flow channels 32 and into the interior cavity 30. The bulbous midsection 44 of the compressed piston 24 may contact the housing 12 at contact point 60 when the piston 24 is compressed. However, fluid may still flow around the piston 24 into the lower flow channel 34. The contact point 60 is not a perfect seal between the piston 24 and the housing 12, but instead may leave crevices and gaps through which the fluid can flow. In other embodiments, grooves or channels may be formed in the interior surface of the housing 12 to facilitate fluid flow around the piston 24. Thus, when the medical implement compresses the piston 24, the fluid can flow from the medical implement through the upper flow channels 32, into the interior cavity 30, around the compressed piston 24, through the lower flow channel 34, through the outlet passage 36, and into the IV tube (not shown).

When the medical implement is removed, the piston 24 expands back into the closed position shown in FIG. 1. As described earlier, the circumferential exterior wall surface 64 of the upper plug section 42 is urged against the upper interior wall 48 of the upper housing section 14. The bulbous midsection 44 of the piston 24 is urged against the tapered wall 56 of the lower housing section 16 and against the shoulder 68 of the upper housing section 14. A first seal point is formed between the upper interior wall 48 and the circumferential exterior wall surface 64 of the piston, and a second seal point is formed between the shoulder 68 and the upper part of the bulbous midsection 44. Thus, fluid communication between the inlet port 28 and the outlet port 26 is terminated, and any fluid in the interior cavity 30 is prevented from flowing back out the inlet port 28 when the medical implement is removed.

When the medical implement compresses the piston 24, as shown in FIG. 4, the volume occupied by the piston 24 decreases, thereby increasing the interior fluid space of the interior cavity 30. This creates a negative displacement which helps to draw in the fluid from the medical implement. When the medical implement is removed, the piston 24 expands in volume, shown in FIG. 1, thereby decreasing the interior fluid space of the interior cavity 30. This causes the valve 10 to flush out the fluid inside the interior cavity 30. The fluid is forced into the lower flow channels 34, through the outlet passage 36, and out the outlet port 26. The valve 10 thus operates as a self-flushing or positive displacement valve. The lower stem section 46 of the piston 24 helps to flush fluid from the valve 10 by occupying volume in the outlet passage 36. The lower stem section 46 thus displaces fluid that would otherwise remain in the outlet passage 36.

Figure 5:
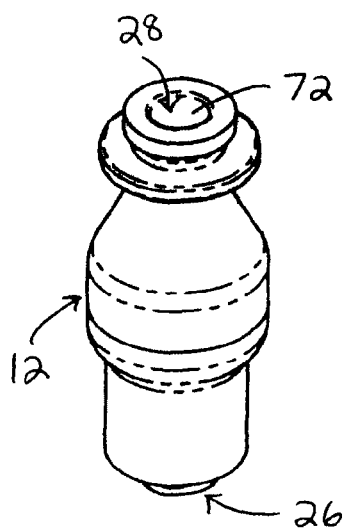
FIG. 5 is a perspective view of the valve of FIG. 4.

Referring now to FIG. 5, a perspective view of the valve of FIG. 4 is shown. The top tapered surface 40 of the piston 24 is not visible through the inlet port 28 because it has been compressed by the medical implement (not shown).

Figure 6:
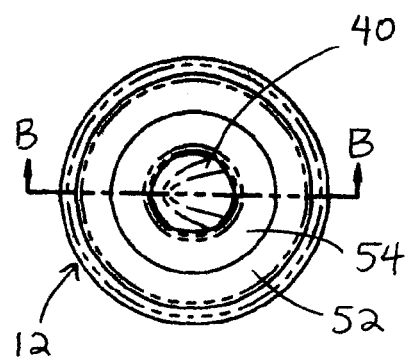
FIG. 6 is a cross-sectional top view of the valve of FIG. 4.

FIG. 6 shows a cross-sectional top view of the valve of FIG. 4. The line BB in FIG. 6 shows the plane of the cross-sectional view of FIG. 4.

Although limited embodiments of the needleless access port valve and its components have been specifically described and illustrated herein, many modifications and variations will be apparent to those skilled in the art. For example, the upper plug section 42 may be over-molded around a hard plastic pin to provide added rigidity, indentations may be formed on the surface of the bulbous midsection 44 to facilitate fluid flow, and the bulbous midsection 44 may be over-molded around a hollow spherical rubber ball to facilitate compression when the piston is urged by a medical implement. Accordingly, it is to be understood that the valve and its components constructed according to principles of this invention may be embodied other than as specifically described herein. The invention is also defined in the following claims.

What is claimed is:

1. A needleless access port valve comprising:
a valve housing comprising an inlet port, an outlet port, and an interior wall surface defining an interior cavity;
a resilient piston made of a homogeneous material positioned within the interior cavity and having a solid upper section of a first diameter, a solid neck section of a second diameter, which is larger than the first diameter, and a mid-section of a third diameter, which is larger than the second diameter;
wherein the interior cavity comprises an upper shoulder, a lower shoulder, and a plurality of flow passages for fluid flow between the piston and the interior wall surface of the housing; and
wherein the neck section is compressed by the upper shoulder for fluid to flow from the inlet port towards the outlet port; the fluid flow being peripheral to the resilient piston; and
wherein the mid-section is compressed by the lower shoulder of the valve housing to terminate fluid communication between the inlet port and the outlet port.

2. The needleless access port of claim 1, wherein the housing comprises an upper housing section, a lower housing section, and an interface therebetween.

3. The needleless access port of claim 1, wherein the piston is made from a silicone elastomer material and is solid throughout.

4. The needleless access port of claim 1, further comprising a stem section extending into the outlet port.

5. The needleless access port of claim 1, further comprising at least one port formed into the resilient piston spaced from an opening of the inlet port.

6. The needleless access port of claim 1, wherein a top surface of the solid upper section comprises a generally flat surface and a tapered surface.

7. The needleless access port of claim 2, further comprising a threaded collar singularly formed to the lower housing section.

8. A needleless access port valve comprising:
a valve housing comprising an inlet port adapted to receive a medical implement, an outlet port, and an interior cavity having an interior surface, an upper shoulder, and a lower shoulder; wherein the upper shoulder comprises one or more upper flow channels, and the lower shoulder comprises one or more lower flow channels; and
a resilient piston made of a homogeneous material positioned within the interior cavity and having a neck section and an enlarged mid-section, and wherein a top surface of the neck section comprises a generally planar surface positioned at an angle to a planar surface defined by an opening of the inlet port when in a closed position;
wherein the neck section is compressed by the upper shoulder and the enlarged mid-section is solid and is compressed by the lower shoulder of the valve housing; and
wherein a flow path is formed between the inlet port and the outlet port and between the interior surface of the valve housing and an exterior surface of the resilient piston when the resilient piston is compressed.

9. The needleless access port of claim 8, wherein the enlarged mid-section of the resilient piston has a contiguous exterior surface without an opening.

10. The needleless access port of claim 9, further comprising a stem section singularly formed to the enlarged mid-section.

11. The needleless access port of claim 8, wherein the piston is made from a silicone elastomer material.

12. The needleless access port of claim 8, wherein the neck section of the resilient piston is of a bore.

13. The needleless access port of claim 8, wherein the resilient piston is solid throughout such that no flow path can form therethrough.

14. A needleless access port valve comprising:
a housing comprising a top opening, an outlet port having a bottom opening, and a hollow interior having an upper raised portion and a lower raised portion, wherein the top opening is adapted to receive a medical instrument and the bottom opening is adapted to communicate with an intravenous tube;
means for biasing located within the hollow interior and formed of a homogeneous material and having a stem projecting from a lower end, wherein the means for biasing is compressed by the upper and lower raised portions of the hollow interior, wherein the means for biasing is adapted to open a fluid pathway between the hollow interior and the medical instrument when the means for biasing is compressed by the medical instrument; and wherein the fluid pathway from the top opening towards the outlet port is peripheral to the means for biasing;
wherein the means for biasing forms a seal with the housing and the stem projects into and occupies at least a portion of the outlet port and the seal prevents fluid flow between the top and bottom openings in a closed position.

15. The needleless access port of claim 14, wherein the housing comprises an upper housing section, a lower housing section, and an interface therebetween.

16. The needleless access port of claim 14, wherein the means for biasing is solid throughout such that no flow path can form therethrough.

17. The needleless access port of claim 14, further comprising at east one port formed into the means for biasing spaced from the top opening.

18. The needleless access port of claim 14, further comprising a flange located distally of the top opening.

19. The needleless access port of claim 15, further comprising a threaded collar singularly formed to the lower housing section.

20. The needleless access port of claim 14, wherein the upper and lower raised portions are flow channels formed into the housing.

* * * * *